United States Patent [19]

Nishizaki

[11] Patent Number: 5,686,252
[45] Date of Patent: Nov. 11, 1997

[54] IMMUNOASSAY METHOD UTILIZING ZETA POTENTIAL AND IMMUNOASSAY KIT

[75] Inventor: Hiroshi Nishizaki, Kawagoe, Japan

[73] Assignee: Hoechst Japan Limited, Tokyo, Japan

[21] Appl. No.: 513,956

[22] PCT Filed: Feb. 25, 1994

[86] PCT No.: PCT/IB94/00039

§ 371 Date: Oct. 23, 1995

§ 102(e) Date: Oct. 23, 1995

[87] PCT Pub. No.: WO94/20853

PCT Pub. Date: Sep. 15, 1994

[30] Foreign Application Priority Data

Mar. 11, 1993 [JP] Japan ................. 5-050257

[51] Int. Cl.⁶ .............................. G01N 33/53
[52] U.S. Cl. .................. 435/7.1; 435/450; 435/489; 435/490; 435/130.1; 435/178.1; 436/531; 436/528; 436/524; 436/519; 436/514; 436/536; 436/808; 436/823; 530/387.1; 530/810; 530/811; 530/812
[58] Field of Search .................. 436/531, 528, 436/524, 519, 514, 536, 808, 823; 435/7.1, 450, 489, 490, 130.1, 178.1; 530/387.1, 810–12

[56] References Cited

U.S. PATENT DOCUMENTS

| | | | |
|---|---|---|---|
| 4,164,558 | 8/1979 | von Schulthess et al. | 436/534 |
| 4,600,698 | 7/1986 | Toth | 436/534 |
| 4,656,144 | 4/1987 | Hosaka et al. | 436/534 |
| 4,843,021 | 6/1989 | Noguchi et al. | 436/533 |
| 4,952,520 | 8/1990 | Okusa et al. | 436/533 |

FOREIGN PATENT DOCUMENTS

| | | |
|---|---|---|
| 0 519 250 A2 | 12/1992 | European Pat. Off. . |
| 2 439 402 | 5/1980 | France . |
| 38 11 102 A1 | 10/1988 | Germany . |

OTHER PUBLICATIONS

Reynolds et al. Infection and Immunity "Effect of Adsorbed Protein on . . . " vol. 39, No. 3, Mar. 1983 pp. 1285–1290.

F.J. Martin et al., "Lipid Vesicle–Cell Interactions", J. Cell Biology, 70(3):494–505 (1976).

*Primary Examiner*—Paula K. Hutzell
*Assistant Examiner*—Heather A. Bakalyar
*Attorney, Agent, or Firm*—Finnegan, Henderson, Farabow, Garrett & Dunner, L.L.P.

[57] ABSTRACT

An immunochemical method is provided for the detection and determination of an analyte. The zeta potential of a latex-particle loaded with an immunologically active substance is measured before and after bringing the loaded latex-particle into contact with an analyte. The difference in zeta potential is correlated with changes of zeta potential for known concentrations of the analyte in order to determine the presence and amount of the analyte.

2 Claims, 1 Drawing Sheet

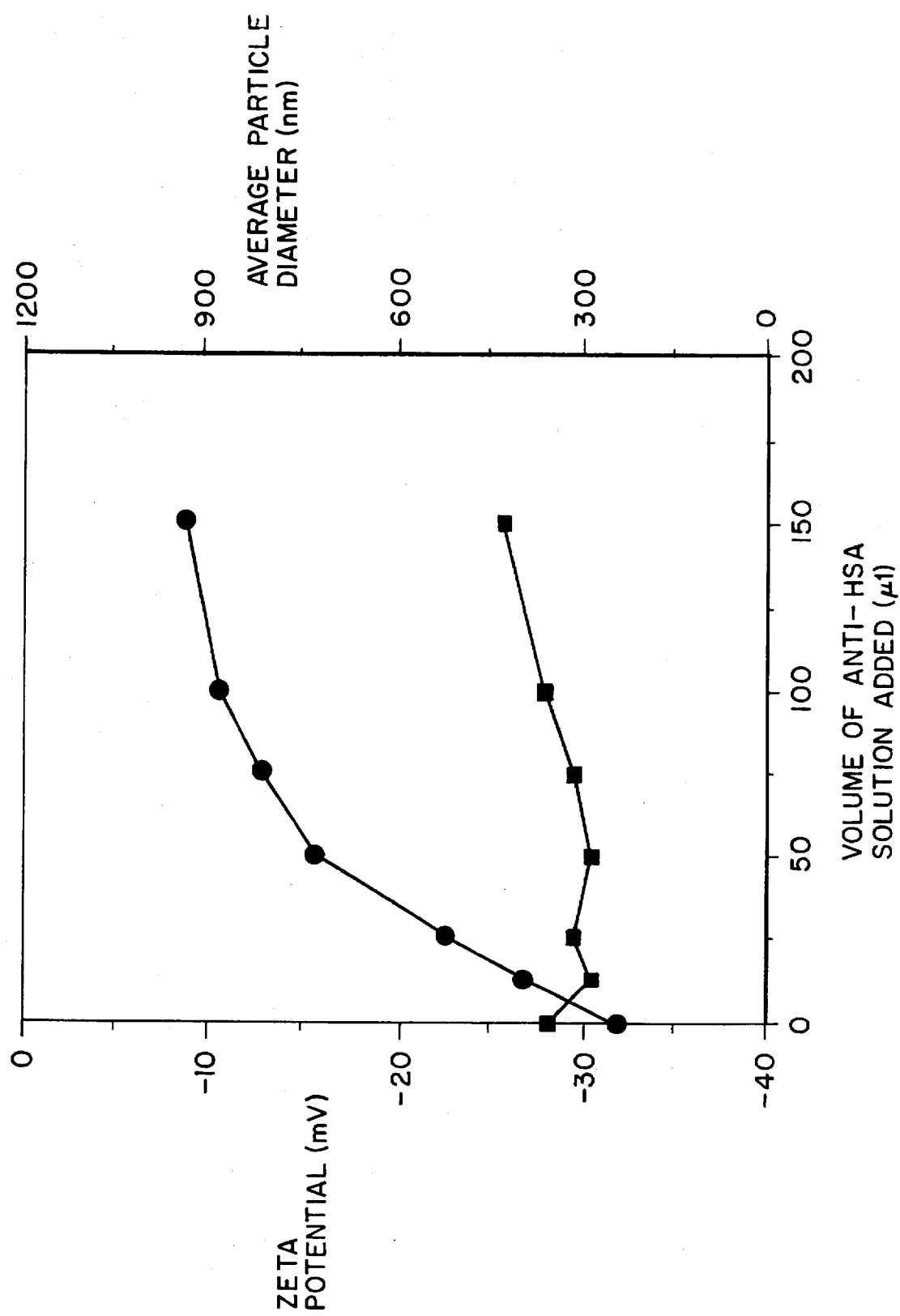

IMMUNOASSAY METHOD UTILIZING ZETA POTENTIAL AND IMMUNOASSAY KIT

BACKGROUND OF THE INVENTION

The present invention relates to an immunoassay method, more particularly to an immunoassay method utilizing zeta potential, which is suitable for quantitative determination of antigens or antibodies and to a test kit which is used in said immunoassay method.

As immunoassay methods utilizing an antigen-antibody reaction, various techniques including agglutination reaction, complement fixation reaction, enzymatic immunoassay, etc. may be used. Of these techniques, the agglutination reaction has been applied for an assay of antibody concentration by fixing a highly specific antibody onto such micro sphere carriers as blood cell particles, bentonite particles, kaolin particles, latex particles and the like, reacting the particles with the corresponding antigen to produce agglutination and determining the said agglutination directly or indirectly. Highly specific antisera could be obtained according to the process of purification techniques of antigens and antibodies. Such an assay is advantageous in that the antigen reacted with the antibody can be readily recovered, as the antibody and others are immobilized onto the micro sphere carrier, this has led to wide application in clinical examinations.

While the agglutination reaction described above is characterized by detecting antigen-antibody reactions depending on agglutination, its drawback is nonspecific agglutination reactions. Therefore, various studies have been made for the purpose of inhibiting such nonspecific agglutination reactions without reducing the efficiency of the specific agglutination reaction (Japanese Unexamined Patent Publication Nos. 146855/1983 and 2163/ 1987).

Further, in order to allow an agglutination reaction to take place at the time of measurement, a specific binding partner immobilized on a micro sphere must be present at least at a predetermined level. Accordingly, stability during storage is diminished, since the antigen has to be present at a relatively high concentration during storage and thus nonspecific agglutination occurs. Various studies are also made to overcome such problems as described above (Japanese Unexamined Patent Publication No. 29149/1988).

The mechanism in the agglutination reaction is a two-step reaction, where an antigen-antibody reaction first takes place and then an agglutination reaction. This gives rise to technical problems, i.e. the difficulty of presetting the conditions for the agglutination reaction and the trouble of changing these conditions depending on a substance to be analyzed.

More specifically, the requirement of agglutination is necessary for agglutination reaction and hence the two drawbacks are presented such as nonspecific agglutination reaction and difficulty in presetting the agglutination reaction conditions.

Therefore, if a reaction between the immunologically active substance immobilized on the micro sphere carrier and the substance which reacts specifically therewith can be detected without an agglutination reaction, the above problems can totally be overcome.

The present inventor has made earnest studies in order to develop the reagent and assay method having a rapid and sensitive immune reaction without undergoing any influence by nonspecific agglutination reaction and others in an immunoassay method, and, as a result, completed the present invention.

SUMMARY OF THE INVENTION

The present invention is directed to an immunoassay method which comprises the steps of bringing a micro sphere carrier carrying an immunologically active substance into contact with a substance which reacts specifically therewith in an aqueous electrolyte solution; measuring zeta potential on the surface of said micro sphere carrier before and after contacting; and correlating any change in said zeta potential with the concentration of said substance which reacts specifically with said active substance and thus determining the presence and/or concentration of said specifically reacting substance.

Moreover, the present invention is directed to a kit used in the immunoassay comprising a vessel containing a suspension of a micro sphere carrier carrying an immunologically active substance; or to an immunoassay kit comprising a vessel containing a micro sphere carrier carrying an immunologically active substance and a vessel containing an aqueous electrolyte solution to suspend the said micro sphere carrier.

In the present invention, the micro sphere carrier preferably is a latex.

The kind of latex particles which may be used in the present invention is not critical and one may use any latex known to those skilled in the art. Latex particles which may be preferably used, are those latexes composed of synthetic polymeric materials such as polystyrene, carboxylated polystyrene, polyvinyl toluene, styrene-butadiene copolymers, carboxylated styrene-butadiene copolymers, styrene-divinyl benzene copolymers, vinyl toluene-tert-butyl styrene copolymers, polyesters, polyacrylate, polymethacrylate, polyacrylonitrile, acrylonitrile-butadiene-styrene copolymers, polyvinyl acetate acrylate, polyvinyl pyrrolidone, vinylchloride-acrylate copolymers and the like.

As the latex particles, there may be preferably used latex particles to which proteins may be coupled by absorption or covalent binding. And further, there may be also used latex particles, the surface of which is treated with a non-ionic detergent. Also preferred are similar synthetic polymeric substances such as bentonite, kaolin, collodion and the like.

The immunologically active substances as used herein are not particularly critical and one may employ any of various antigens and antibodies which may be applied in immuno reaction. Examples of those immunologically active substances are for instance immunoglobulins, rheumatic factors, antinuclear factor, human albumin, anti-human albumin antibody, streptolysin O, anti-streptolysin O antibody, C-reactive protein, anti-C-reactive protein antibody, α-fetoprotein (AFP), anti-AFP antibody, carcinoembryonic antigen (CEA), anti-CEA antibody, human placental lactogen (HPL), anti-HPL antigen, human chorionic gonadotropin (HCG), anti-HCG antigen, anti-estrogen antibody, anti-insulin antibody, hepatitis B surface antigen (HBS), anti-HBS antigen, treponema palliadum antigen, rubella antigen, complement component C1q, anti-complement component C1q antibody and the like.

The zeta potential as used herein is defined as the potential difference induced at the interface between a charged solid material and an aqueous electrolyte solution when contacted. The correlation between zeta potential and agglutination of solid particles has been discussed, for instance the zeta potential of a latex surface has been utilized as the standard to confirm performance of a polymer latex (Japanese Unexamined Patent Publication No. 26603/1989). The correlation between the zeta potential of the cell surface of erythrocytes and agglutination of erythrocytes has been mentioned (J. Cell. Biol., Vol. 70, 1976, 494–505).

The instant invention is based on the concept of determining the concentration of a substance which reacts specifically with said active substance by measuring the zeta potential on the surface of the micro sphere carrier carrying an immunologically active substance.

It is an object of the present invention to determine quantitatively the substance to react with an immunologically active substance carried on a micro sphere carrier upon changes in zeta potential. The zeta potential may change from the positive potential side to negative potential side or from negative potential side to positive potential side. And further, the change may be brought about only in the range of positive potential or only in the range of negative potential.

The aqueous electrolyte solution is not particularly critical to suspend the micro sphere carrier carrying an immunologically active substance and one may use an aqueous electrolyte solution commonly used for suspension of micro sphere carriers such as a solution of sodium chloride or potassium chloride dissolved in a phosphate buffer. A concentration of the electrolyte is preferably 0.02–0.5% (w/v), more preferred is a concentration of 0.04 to 0.1% (w/v).

As the vessel containing a suspension of a micro sphere carrier carrying an immunologically active substance in an aqueous electrolyte solution or a vessel to contain the electrolyte solution, one may use a plastic or glass bottle or ampoule.

The method of the present invention can be performed by conventional procedures: a micro sphere carrier loaded with an immunologically active substance is suspended in an aqueous electrolyte solution; the zeta potential of the resulting suspension is determined; a substance (to be analyzed) which reacts specifically with said immunologically active substance is added to the suspension and stirred; the zeta potential of the resulting suspension is measured; and the difference between these two zeta potential values is correlated with the concentration of the substance to be analyzed.

BRIEF DESCRIPTION OF THE DRAWING

FIG. 1 shows a graph illustrating the relationship between the concentration of the substance to be analyzed and the zeta potential, wherein the relationship between the concentration of the substance to be analyzed and the zeta potential is plotted by closed circles, while the relationship between the concentration of the substance to be analyzed and average diameter of the particles in suspension is plotted by closed squares.

DESCRIPTION OF THE PREFERRED EMBODIMENT

The present invention will be illustrated by way of the following example, but it will not be limited to the example below.

Example 1 a) Method of the preparation of latex particles immunized with human serum albumin (HSA)

A commercially available latex suspension (Behringwerke A.G., a carboxyl group type, a diameter of 276 nm) was diluted with a 0.01M phosphate buffer (pH 8.2) to form a suspension having a concentration of 2.5% (w/v). To 4 ml of this suspension 0.5 ml of a phosphate buffer containing HSA at 1% was added and, after stirring, the mixture was cooled at 10° C. for 10 minutes. To the mixture was added 0.5 ml of a phosphate buffer containing carbodiimide at 1% (w/v) which was previously cooled at 10° C. and, while stirring again, 0.1N hydrochloride was added dropwise to adjust a pH value to 5.0. The reaction mixture was stirred at 10° C. for a further 2 hours and centrifuged to give a HSA-immunized latex precipitate. To the precipitate was added 10 ml of 0.1M phosphate buffer (pH 7.0) the mixture was resuspended and then sonicated to prepare a 1% homogenous suspension of HSA-immunized latex particles. The HSA-immunized latex particle suspension under the present condition was stored at a low temperature (preferably 4° to 10° C.).

b) Determination of zeta potential and average particle diameter of HSA-immunized latex particles before and after reaction with anti-HSA antibody A 1% suspension of HSA-immunized latex particles as prepared in (1a)) was diluted with 10 mM aqueous sodium chloride solution to a concentration of 0.0001% (w/v) and used for measurement. To 10 ml of the thus diluted 0.0001% suspension of HSA-immunized latex particles was added a solution prepared by diluting a commercially available 1.9% (w/v) solution of anti-HSA-antibody with a 10 mM aqueous sodium chloride solution to a concentration of 0.001% (w/v) in amounts of 0, 13, 25, 50, 75, 100 and 150 μl, respectively, to effect reaction at room temperature for 2 hours. Hereinafter the zeta potential and average particle diameter of the latex particles were measured using a laser zeta potential meter LEZA-600 (manufactured by Ohtsuka Electronics K. K.). The results are as shown in FIG. 1.

The results in FIG. 1 show that change in the zeta potential can be observed depending on the concentration of the substance to be analyzed with no change in the average particle diameter of the latex particles, i.e. without an agglutination reaction between the particles, which demonstrates the utility of the present method.

c) Study on stability during storage

The HSA-immunized latex particle suspension was prepared in the same manner as described in (1 a)) and diluted with 0.1M phosphate buffer to form a 0.01% (w/v) suspension, which was then stored at a low temperature. The zeta potential and average particle diameter were measured in the same way as described in Example 2 using the suspension and similar results were obtained, which showed no nonspecific agglutination reaction brought about even during storage The immunoassay of the present invention is a method employing change in the zeta potential of the micro sphere carrier loaded with an immunologically active agent and enjoys the speed and sensitivity specific to immunological reactions. Besides, the present method employs no agglutination reaction unlike the conventional immunoassay, so that it is free from not only the disadvantageous nonspecific agglutination reaction but also of the difficulty of presetting the conditions for the agglutination reaction.

Further, according to the method of the present invention, nonspecific reactions can be inhibited due to the low particle concentration in the assay as compared with that in methods using agglutination reaction. Nonspecific agglutination reactions during storage can also be inhibited, since the particles can be stored at a relatively low concentration.

What is claimed is:

1. An immunochemical method for the detection and determination of an analyte comprising the steps of:

a) measuring the zeta potential of a latex-particle loaded with an immunologically active substance being capable of specifically reacting with the analyte suspended in an aqueous electrolyte solution;

b) bringing into contact the latex-particle loaded with an immunologically active substance with the analyte;

c) measuring the zeta potential of the latex-particle loaded with an immunologically active substance to which the analyte is bound;

d) correlating the difference in the zeta potential with changes of zeta potential for known concentrations of the analyte and thereby determining the presence and amount of the analyte.

2. The method according to claim 1, wherein said immunologically active substance or said analyte is an immunoglobulin.

* * * * *